US010625066B2

(12) United States Patent
Kantrowitz

(10) Patent No.: US 10,625,066 B2
(45) Date of Patent: Apr. 21, 2020

(54) VACUUM ASSISTED PERCUTANEOUS APPLIANCE

(71) Applicant: VIADERM, LLC, Ann Arbor, MI (US)

(72) Inventor: Allen B. Kantrowitz, Ann Arbor, MI (US)

(73) Assignee: Viaderm, LLC, Ann Arbor, MI (US)

( * ) Notice: Subject to any disclaimer, the term of this patent is extended or adjusted under 35 U.S.C. 154(b) by 162 days.

(21) Appl. No.: 15/312,791

(22) PCT Filed: May 26, 2015

(86) PCT No.: PCT/US2015/032434
§ 371 (c)(1),
(2) Date: Nov. 21, 2016

(87) PCT Pub. No.: WO2015/179862
PCT Pub. Date: Nov. 26, 2015

(65) Prior Publication Data
US 2017/0189663 A1 Jul. 6, 2017

Related U.S. Application Data

(60) Provisional application No. 62/002,322, filed on May 23, 2014.

(51) Int. Cl.
A61M 39/02 (2006.01)
A61M 25/02 (2006.01)
A61M 1/28 (2006.01)

(52) U.S. Cl.
CPC .......... A61M 39/0247 (2013.01); A61M 1/28 (2013.01); A61M 25/02 (2013.01);
(Continued)

(58) Field of Classification Search
CPC ........ A61M 39/0247; A61M 2039/025; A61M 2039/0252; A61M 2039/0276;
(Continued)

(56) References Cited

U.S. PATENT DOCUMENTS 4,496,349 A * 1/1985 Cosentino ......... A61M 39/0247
128/899
4,634,422 A 1/1987 Kantrowitz et al.
(Continued)

FOREIGN PATENT DOCUMENTS

EP 0113520 A2 7/1984
JP S5892360 A 6/1983
(Continued)

OTHER PUBLICATIONS

Sissons, C.H., Wong, L., and Cutress, T.W., "Inhibition by Ethanol of the Growth of Biofilm and Dispersed Microcosm Dental Plaques", Archives of Oral Biology, Jan. 1996, pp. 27-34, vol. 41, issue 1, Copyright Elsevier Science Ltd. (1996).
(Continued)

Primary Examiner — Lauren P Farrar
Assistant Examiner — James D Ponton
(74) Attorney, Agent, or Firm — Blue Filament Law PLLC

(57) ABSTRACT

A luminal access device is provided that includes a luminal graft attached to a patient lumen. A percutaneous access device (PAD) is coupled to the luminal graft and adapted to stabilize a conduit in fluid communication with the luminal graft and an external medical device. A portion of said PAD adapted to be external to the patient and seal around said conduit. Infectious agent penetration at an insertion site of the PAD is reduced by providing a porous inner sleeve fluidly connected to a conduit. A vacuum or hydrodynamic source is fluidly connected to the conduit to create a fluid draw from the subject tissue through the inner sleeve to the conduit. The conduit is readily formed to have a bore and an outer conduit surface, the outer conduit surface being optionally nanotextured. The conduit bore is adapted to accommodate a medical appliance.

18 Claims, 6 Drawing Sheets

(52) U.S. Cl.
CPC .............. *A61M 2025/0293* (2013.01); *A61M 2039/025* (2013.01); *A61M 2039/027* (2013.01); *A61M 2039/0255* (2013.01); *A61M 2039/0258* (2013.01); *A61M 2039/0273* (2013.01); *A61M 2039/0276* (2013.01); *A61M 2039/0288* (2013.01); *A61M 2210/0693* (2013.01); *A61M 2210/1078* (2013.01)

(58) Field of Classification Search
CPC .. A61M 2039/0279; A61M 2039/0285; A61M 2039/0288; A61M 2039/0255; A61M 2039/0258; A61M 2039/0261; A61M 2039/027; A61M 2039/0273; A61M 1/28; A61M 25/02; A61M 2025/0293
See application file for complete search history.

(56) References Cited

U.S. PATENT DOCUMENTS

| | | | |
|---|---|---|---|
| 4,668,222 A | | 5/1987 | Poirier |
| 5,059,186 A | | 10/1991 | Yamamoto et al. |
| 5,120,313 A | | 6/1992 | Elftman |
| 5,250,025 A | | 10/1993 | Sosnowski et al. |
| 5,405,388 A | * | 4/1995 | Fox .................. A61B 10/00 623/16.11 |
| 5,814,058 A | | 9/1998 | Carlson et al. |
| 5,874,500 A | | 2/1999 | Rhee et al. |
| 5,997,524 A | | 12/1999 | Burbank et al. |
| 6,056,970 A | | 5/2000 | Greenawalt et al. |
| 6,231,541 B1 | * | 5/2001 | Kawamura ....... A61M 39/0247 604/175 |
| 6,503,228 B1 | | 1/2003 | Li et al. |
| 6,524,273 B2 | * | 2/2003 | Kawamura ......... A61M 1/3655 604/175 |
| 6,656,496 B1 | | 12/2003 | Kilpadi et al. |
| 7,704,225 B2 | | 4/2010 | Kantrowitz |
| 8,202,310 B2 | | 6/2012 | Majercak et al. |
| 8,845,573 B2 | | 9/2014 | Hausler et al. |
| 8,974,422 B2 | | 3/2015 | Gill et al. |
| 9,295,773 B2 | | 3/2016 | Prosl et al. |
| 2003/0233023 A1 | | 12/2003 | Khaghani et al. |
| 2006/0276837 A1 | * | 12/2006 | Bergin ............... A61B 17/0057 606/213 |
| 2009/0277850 A1 | * | 11/2009 | Adams ................ A61M 1/1678 210/798 |
| 2009/0287145 A1 | | 11/2009 | Cragg et al. |
| 2010/0042070 A1 | * | 2/2010 | Gill .................. A61M 39/0247 604/513 |
| 2010/0152640 A1 | * | 6/2010 | Golding ............ A61M 39/0247 604/6.16 |
| 2011/0288534 A1 | * | 11/2011 | Aguirre ............... A61J 15/0015 604/535 |
| 2012/0310181 A1 | * | 12/2012 | Kantrowitz ....... A61M 39/0247 604/264 |
| 2013/0261531 A1 | | 10/2013 | Gallagher et al. |
| 2014/0024998 A1 | | 1/2014 | Prosl et al. |

FOREIGN PATENT DOCUMENTS

| | | |
|---|---|---|
| JP | H11502750 A | 3/1999 |
| JP | 2010510016 A | 4/2010 |
| JP | 2013520243 A | 6/2013 |
| JP | 2013526340 A | 6/2013 |
| WO | 2008060380 A2 | 5/2008 |
| WO | 2008062173 A1 | 5/2008 |

OTHER PUBLICATIONS

Saint, S., Veenstra, D.L., and Lipsky, B.A., "The Clinical and Economic Consequences of Nosocomial Central Venous Catheter-Related Infection: Are Antimicrobial Catheters Useful?", Infection Control and Hospital Epidemiology, Jun. 2000, pp. 375-380, vol. 21, issue 6, Copyright the Society for Healthcare Epidemiology of America (2000).

Safdar, N. and Maki, D.G., "The pathogenesis of catheter-related bloodstream infection with noncuffed short-term central venous catheters", Journal of Intensive Care Medicine, Jan. 2004 (Published online: Nov. 26, 2003), pp. 62-67, vol. 30, issue 1, Copyright Springer-Verlag (2003).

Norman, J.J. and Desai, T.A., "Control of Cellular Organization in Three Dimensions Using a Microfabricated Polydimethylsiloxane—Collagen Composite Tissue Scaffold", Tissue Engineering., Mar.-Apr. 2005, pp. 378-386, vol. 11, issues 3-4, Copyright Mary Ann Liebert, Inc. (2005).

International Search Report dated Sep. 1, 2015 for International Application No. PCT/US2015/032434 filed May 26, 2015.

Supplementary European Search Report dated Mar. 14, 2018 for European Application No. 15795827 filed May 26, 2015.

English translation of First Notice of Reasons for Refusal dated Dec. 10, 2018 for Japanese Application No. 2017-514398 filed May 26, 2015.

English translation of Second Notice of Reasons for Refusal dated May 9, 2019 for Japanese Application No. 2017-514398 filed May 26, 2015.

* cited by examiner

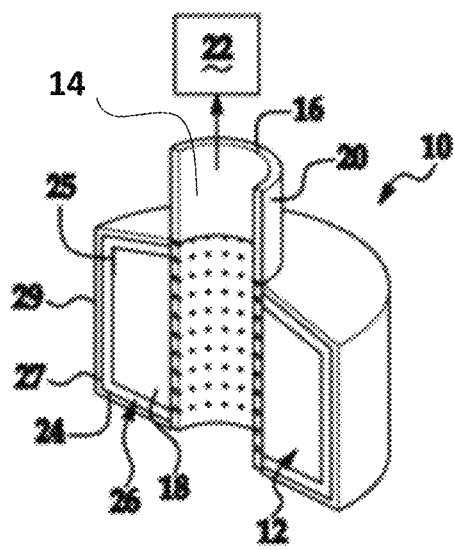
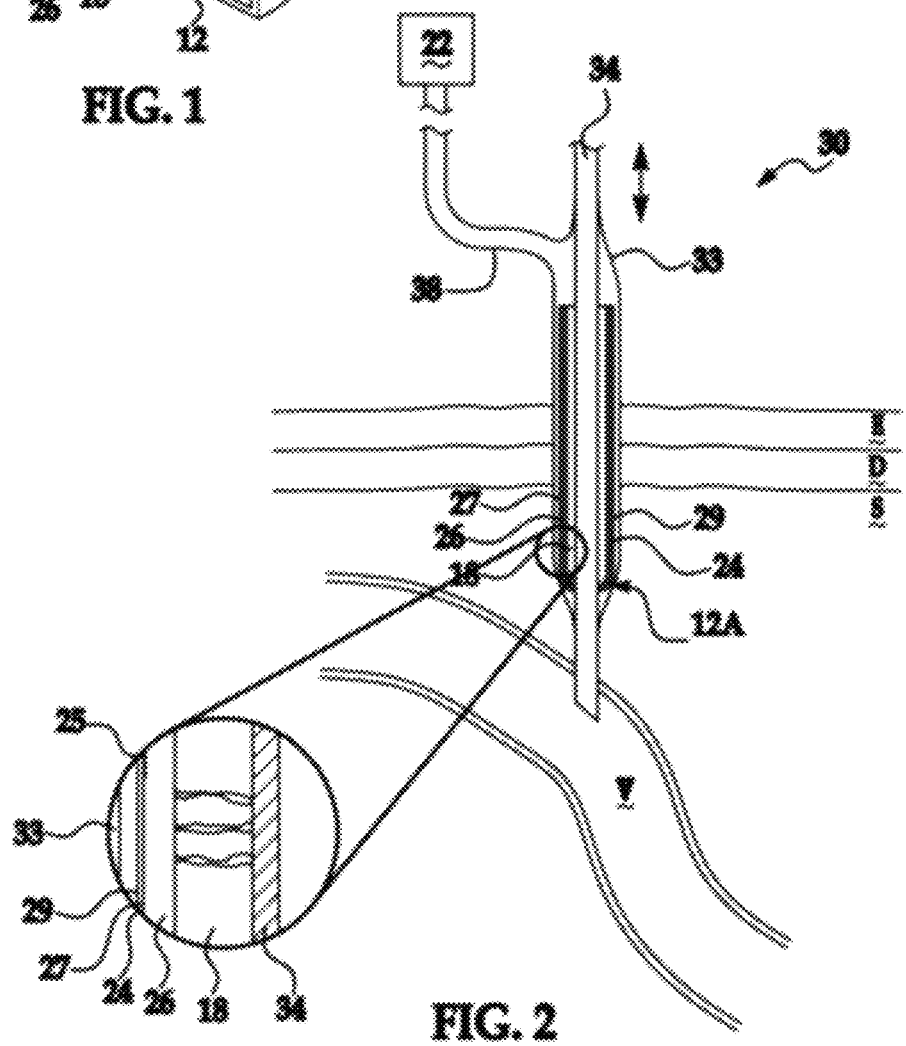

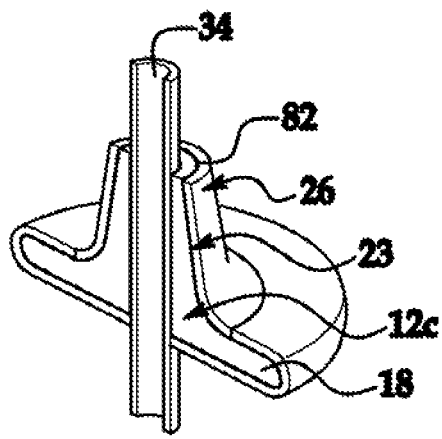
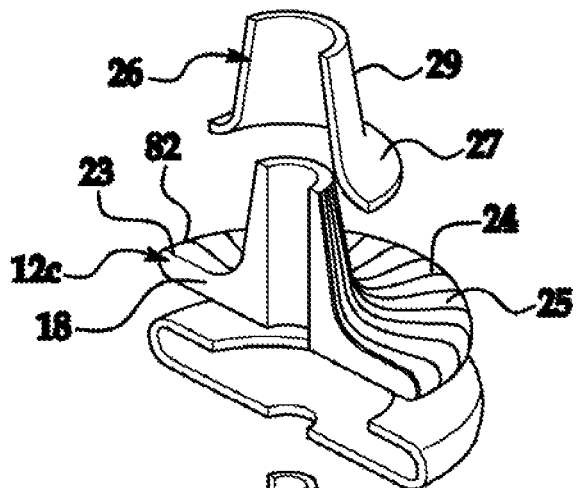
FIG. 8A
FIG. 8B
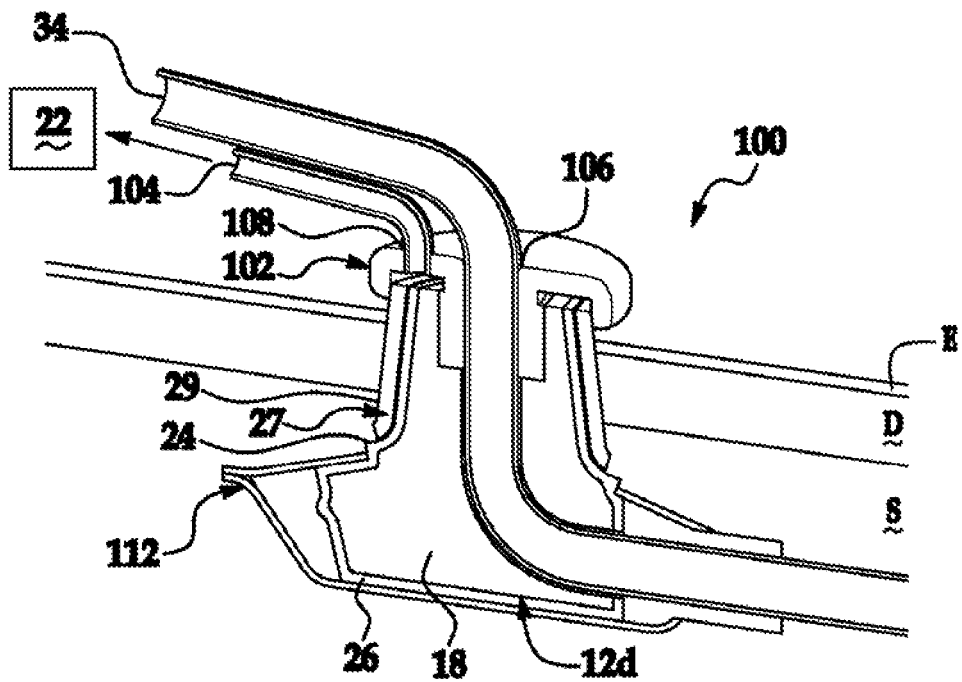
FIG. 9

VACUUM ASSISTED PERCUTANEOUS APPLIANCE

RELATED APPLICATIONS

This application claims priority benefit of U.S. Provisional Application Ser. No. 62/002,322 filed May 23, 2014; the contents of which are hereby incorporated by reference.

FIELD OF THE INVENTION

The invention relates in general to percutaneous access and in particular to processes and devices for preventing infection at the site of percutaneous access. More specifically, the invention provides processes and devices for preventing internalization of bacteria, other infectious agents, or other unwanted materials from entering the access point for an intraluminal device.

BACKGROUND OF THE INVENTION

Intravenous catheters act as an attachment point for microorganisms, leading to biofilm formation and infection at the site of insertion or along the surface of the device. Infection of the catheter hub and catheter-related bloodstream infections are major complications for patients with indwelling catheters (e.g., Safdar and Maki, *Intensive Care Med.* 2004 January; 30(1):62-7; Saint et al., *Infect Control Hosp Epidemiol.* 2000 June; 21(6):375-80).

Prior attempts at controlling catheter-related infection are directed to sterilization techniques such as by topical or fluidic antibacterials applied to the insertion site or integrated into the catheter itself. The antimicrobial activity of ethyl alcohol (ethanol) as well as other alcohols is well known. Isopropyl alcohol at a concentration of 60-70% is widely used as an antimicrobial agent for sanitization of surfaces and skin. A concentration of 10% ethyl alcohol inhibits the growth of most microorganisms, while concentrations of 40% and higher are generally considered bactericidal (Sissons et al., *Archives of Oral Biology*, Vol. 41, 1, JN 1996; 27-34).

Catheterization can be kept in place for as little as a few seconds for drainage or delivery. It is increasingly common, however, for percutaneous access such as peripherally inserted central catheters (PICC), skeletal guide wires, cardiac assist device lines, or other instruments to be kept in place for weeks or months. The increased time in which such devices are maintained across the skin increases the likelihood of instrument related infection.

Thus, there exists a need for processes and devices to prevent or reduce the likelihood of infection related to percutaneous instruments.

SUMMARY OF THE INVENTION

A luminal access device is provided that includes a luminal graft attached to a patient lumen. A percutaneous access device (PAD) is coupled to the luminal graft and adapted to stabilize a conduit in fluid communication with the luminal graft and an external medical device. A portion of said PAD adapted to be external to the patient and seal around said conduit. Infectious agent penetration at an insertion site of the PAD is reduced by providing a porous inner sleeve fluidly connected to a conduit. A vacuum or hydrodynamic source is fluidly connected to the conduit to create a fluid draw from the subject tissue through the inner sleeve to the conduit. The conduit is readily formed to have a bore and an outer conduit surface, the outer conduit surface being optionally nanotextured. The conduit bore is adapted to accommodate a medical appliance. The sleeve in fluid communication with the conduit is readily formed of materials characterized by a pore matrix through which vacuum or hydrodynamic draw is achieved without collapse under the vacuum or hydrodynamic draw conditions.

A process for stabilizing an implanted device at a percutaneous insertion site in subject tissue includes inserting the aforementioned device subcutaneously and drawing vacuum against the subject tissue at the insertion site through the sleeve and the conduit or fluid from the insertion site through said conduit to draw fibroblasts into and onto said sleeve to stabilize the implanted device.

A kit for reducing agent penetration at a percutaneous insertion site in subject tissue is provided that includes a gasket connecting to a percutaneous access device and a bandage attached to the gasket to form a pressure-tight seal around the insertion site. A conduit associated with the percutaneous access device is in fluid communication with the bandage and the subject tissue surrounding the insertion site. A vacuum or hydrodynamic draw against the conduit serves to reduce agent penetration at the percutaneous insertion site in the subject tissue.

BRIEF DESCRIPTION OF THE DRAWINGS

FIG. 1 is a cross-sectional view of an inventive device with the relative dimensions of aspects exaggerated for visual clarity;

FIG. 2 is a cross-sectional view of an inventive device with relative dimensions of aspects exaggerated for visual clarity depicting an outer sleeve covering an inner sleeve for protection during skin penetration;

FIG. 8A is a perspective cross-sectional view of percutaneous components of inventive device with relative dimensions of aspect exaggerated for visual clarity depicting a flanged inner sleeve and an optional open-celled, implant compatible velour cuff;

FIG. 8B is an exploded view of FIG. 8A;

FIG. 9 is a partial cutaway view of a flanged inventive device with relative dimensions of aspect exaggerated for visual clarity

DETAILED DESCRIPTION OF THE PREFERRED EMBODIMENTS

Figure 3:
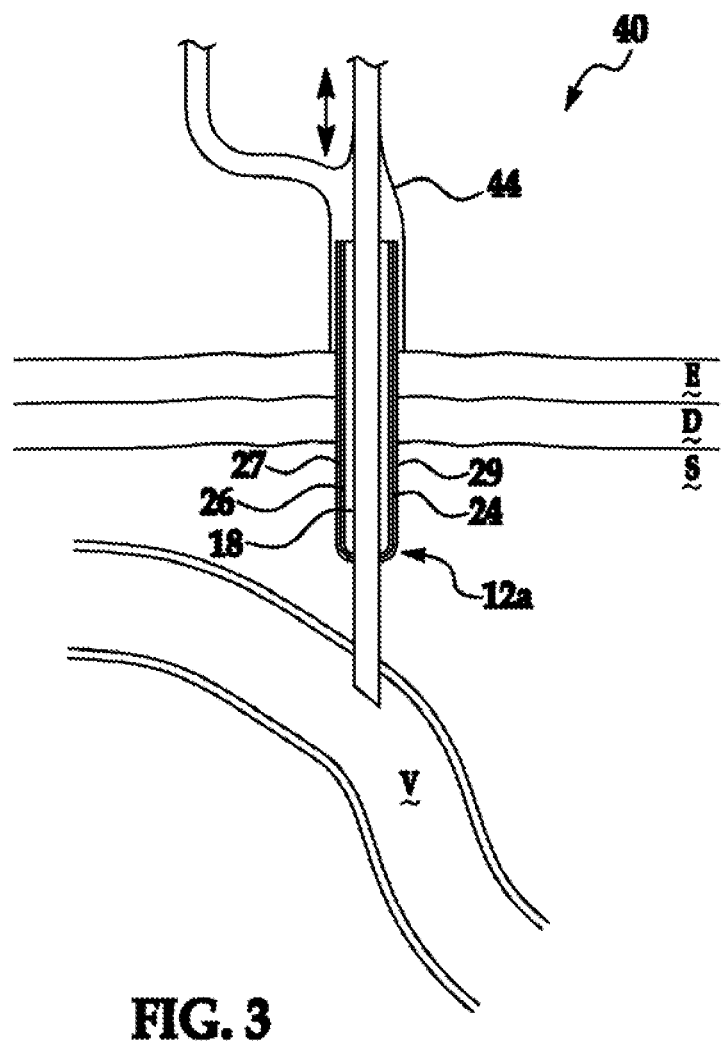
FIG. 3 is a cross-sectional view of an inventive device with relative dimensions of aspects exaggerated for visual clarity depicting a skin surface terminating outer sleeve.

The following description of the preferred embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. The inventive devices are disclosed herein in general with respect to a catheter, but this is not meant to be a limitation on the invention. Any tube, instrument, wire, material or assembly that penetrates the skin of a subject is similarly operable for use with the inventive device or integral therewith.

The invention has utility as a device to reduce the likelihood of percutaneous instrument related infection.

An inventive device is intended for use with a percutaneous instrument. Any instrument that is intended to traverse the skin is operable with the inventive device. The device is optionally used with a percutaneous access device illustratively a PICC, cannula, or other catheter, or pin illustratively a Steinman pin, Kirschner wires, and other devices or instruments that penetrate the skin. It is appreciated that the device is similarly operable with bladder or other catheterization instrument.

The inventive devices decrease or prevent penetration or complications due to the presence of an agent. As used herein an "agent" is illustratively: an infectious agent such as bacteria, virus, fungus, other organism; or foreign material. Illustrative examples of foreign material include: bandage; soil; water, saliva, urine, or other fluid; feces; chemicals; or other matter known in the art. Illustrative examples of infectious agents that are prevented from penetrating or produce complications include *P. aeruginosa, E. cloacae; E. faecalis; C. albicans; K. pneumonia; E. coli; S. aureus*; or other infectious agents.

An inventive device is optionally used on the epidermis of a subject. As used herein, the term "subject" refers to a human or non-human animal, optionally a mammal including a human, non-primate such as cows, pigs, horses, goats, sheep, cats, dogs, avian species and rodents; and a non-human primate such as monkeys, chimpanzees, and apes; and a human, also denoted specifically as a "human subject".

An inventive device illustratively operates by providing a force to counteract fluid collection or flow along a percutaneous instrument-tissue interface. It is common for fluid to develop in the space surrounding a percutaneous instrument often beginning immediately after insertion. The presence of this fluid allows migration, flow, or other penetration of agents normally excluded by the intact skin to areas below the skin. The penetration by these agents may lead to development of infectious disease, inflammation at the site of insertion, or other unwanted complications.

As used herein, an "insertion site" is defined as an intentional interruption of skin or other tissue for the placement of a medical appliance.

A force is illustratively a vacuum. A vacuum illustratively prevents fluid from moving along an interface between tissue and the embedded catheter or other instrument. The negative pressure of the vacuum allows the natural pressures of biological material or other atmospheric pressure to move unwanted material away from the areas at or below the site of insertion.

An inventive device includes one or more sleeves. A sleeve is optionally an inner sleeve or an outer sleeve. As used herein, the terms "inner" and "outer" are relative terms in terms of encompassing relative dimensions and should not be construed contextually as to positioning relative to the epidermis. An inner sleeve is optionally made of a porous material or scaffold that is optionally penetrated by fluids or gasses. A scaffold is optionally a tissue scaffold that allows or promotes attachment of cells, illustratively, fibroblasts to the surface of an inner sleeve. An inner sleeve is optionally treated. An inner sleeve treatment illustratively includes compounds or surface textures that promote attachment of fibroblasts or other cellular material. Optionally, the inner sleeve is made of a woven material. A woven material is optionally penetratable by cells, fluids, gas, or other materials.

It is appreciated that an inner sleeve is optionally the only sleeve present in the device. An inner sleeve is optionally a porous scaffold that is suitable for moving fluid or gas through the sleeve away from the surrounding environment. Materials operable for use as an inner sleeve illustratively include: collagen, PEBAX, nylons, polypropylenes, polyurethanes, polyethylenes (HDPE, UHWPE, LDPE, or any blend of the aforementioned polyethylenes), PET, NiTi, MYLAR, Nickel Titanium Alloy, other polymers such as other thermoplastic polymers, fabrics, silicones such as silicone rubber, latex, glass, or other materials known in the art. It is appreciated that polymeric materials with a gradient of cross-linking density through the material afford certain advantages with respect to promoting vacuum or hydrodynamic draw and fibroblast infiltration. By way of example, a polymer having a greater rigidity proximal to the central axis of the device relative to the distal surface inhibits pressure differential induced collapse. In some embodiments, an inner sleeve is made from chemically inert material. In some embodiments, the porous scaffold is in direct contact with the skin of the subject or traverses the skin of the subject. In some embodiments an inner sleeve is textured or woven in such a way so as to provide attachment sites for fibroblasts. A texture is optionally a nanotexture. Illustrative nanotextures have pore sizes that are uniformly less than 500 nanometers to provide an anchor point for a fibroblast pseudopod extension, while having dimensions that disfavor bacterial colonization. A nanotextured surface as used herein has features indentations of from 50 to 500 nanometer median dimension. In some embodiments, the indentations have a median dimension of between 100 and 300 nanometers.

In some embodiments, a texture is in the form of a scaffold. A scaffold is illustratively formed of gold. A gold scaffold is optionally formed by making a sleeve from a gold/silver alloy that is dipped in an acid such as a mineral acid which selectively dissolves the silver leaving a gold structure with appropriate porosity. Alternatively, a scaffold is formed from an acid etchable, biocompatible nanocrystal such as silver or silica is dispersed in a polymer melt such as polycarbonate and a neck either formed directly therefrom, or the nanocrystal-doped polymer is coated onto a neck substrate. Through subjecting the nanocrystal-doped polymer to an acid or base solution, depending on the solubility of the nanocrystal, voids are formed in the polymer reflective of the original nanocrystal dopant. For instance, silver is readily dissolved in 6 N hydrochloric acid while silica is dissolved in concentrated hydrofluoric acid. Dissolution in the presence of sonication is appreciated to facilitate the process. Nanocrystal loading of 1 to 10 percent by weight, depending on the specific nanocrystal dimensions, is sufficient to achieve the desired uniformity and density of pores. Other porous surfaces and methods of manufacture are illustrated in U.S. Pat. No. 7,704,225 and references cited therein, each of which are incorporated herein by reference in their entirety.

It is appreciated that an inner sleeve is optionally coated or impregnated with a first compound. Coating or impregnating optionally provides lubrication so as to ease insertion of the instrument into the skin. A compound optionally: is antibacterial such as those described in WO 2008/060380, the contents of which are incorporated herein by reference; resist or promote cellular adhesion; are anticoagulants or procoagulants; or other desirable compound.

A compound optionally includes factors operable to selectively promote fibroblast growth and/or decrease attachment of bacteria or other contaminants. A compound optionally promotes growth of cells such as fibroblasts. A coating optionally includes the compound fibroblast growth factor (FBF). Optionally, FBF is used in a coating along with insulin and/or dexamethasone. The presence of dexamethasone and/or insulin will promote multiple layer growth of fibroblasts on the surface of or within the pores of a sleeve.

Coating substances illustratively include cell growth scaffolding matrices as detailed in U.S. Pat. Nos. 5,874,500; 6,056,970; and 6,656,496; and Norman et al. *Tissue Eng*. March 2005, 11(3-4) pp. 375-386, each of which is incorporated herein by reference. An exemplary coating is a tissue scaffolding, poly-p xylylene, parylene and chemical modified versions of such coatings to enhance post-insertion stabilization. Chemical modifications illustratively include bonding of fibronectin and other molecules implicated in the healing process. While tissue scaffolding and polymers are readily applied by painting, dip coating and spraying, it is also appreciated that polymeric coating are also readily applied by gas phase deposition techniques such as chemical vapor deposition (CVD). A coating is optionally porous in order to enhance capillary draw. In some embodiments a coating is biodegradable. A coating optionally has pores typically of an average size of between 10 and 500 microns, optionally, of an average size of between 30 and 50 microns.

An inventive device optionally includes an outer sleeve. An outer sleeve functions to segregate or deliver vacuum draw pressure to an inner sleeve. The outer sleeve optionally circumferentially and longitudinally covers an inner sleeve. This configuration optionally shields the inner sleeve from epidermal bacterial or other agents upon insertion.

An outer sleeve is optionally tapered at one or both ends. Tapering at a distal end (the end nearest the internal end of the catheter during use) provides improved insertion of the instrument into the skin of a subject. A taper may form a smooth interaction with the catheter at the outer sleeve distal end or a ridge is optionally present at or near the site of device interaction with the catheter.

An outer sleeve is optionally made of any material suitable for use with a percutaneous instrument. Illustrative materials operable for an outer sleeve include such materials that have a memory or are self-expanding. Materials operable for use as an outer sleeve illustratively include: PEBAX, nylons, polyurethanes, polyethylenes (HDPE, UHWPE, LDPE, or any blend of the aforementioned polyethylenes), PET, NiTi, MYLAR, Nickel Titanium Alloy, other polymers such as other thermoplastic polymers, fabrics, silicones such as silicone rubber, latex, glass, or other materials known in the art. An outer sleeve optionally includes or is formed of a scaffold. An outer sleeve scaffold is optionally made of the same or different material as an inner sleeve scaffold. Scaffolds operable for an inner sleeve are similarly operable for an outer sleeve.

An outer sleeve is optionally expandable. An expandable outer sleeve is optionally by stretch of the material, unfolding of the material illustratively like of an accordion or other mechanism, or material that will provide expandability or compressibility to the outer sleeve.

It is appreciated that an outer sleeve is optionally coated or impregnated with a second compound. A second compound is optionally the same as a first compound. Coating or impregnation optionally provides lubrication so as to ease insertion of the instrument into the skin. A compound optionally: is an antibacterial coating or impregnated material such as those described in WO 2008/060380, the contents of which are incorporated herein by reference compounds to resist or promote cellular adhesion; anticoagulants or procoagulants; or other desirable compound.

In some embodiments, an outer sleeve is textured. A texture is optionally formed of a tissue scaffold. A texture on an outer or inner sleeve optionally has pore sizes, ridges, depressions, indentations, or other texture that is uniform or non-uniform. A texture is optionally of a depth less than 500 nanometers to provide an anchor point for a fibroblast pseudopod extension, while having dimensions that disfavor bacterial colonization. A nanotextured surface as used herein has a uniform distribution of 50 to 500 nanometer median dimension indentations. In some embodiments, the indentations have a median dimension of between 100 and 300 nanometers.

In some embodiments an outer sleeve surrounds an inner sleeve. The outer sleeve and inner sleeve are optionally formed from a unitary piece of material. The outer sleeve is optionally oriented surrounding an inner sleeve and optionally is slidably positionable about an inner sleeve. In some embodiments an outer sleeve protects an inner sleeve upon insertion of the inventive instrument and is positionally adjusted relative to the inner sleeve illustratively to a mark or other region that is optionally positioned above the epidermis. In some embodiments the inner sleeve remains traversing the skin while the outer sleeve is positioned above the epidermis or penetrates to one or more desired depths or levels.

An outer sleeve is optionally positioned external to the skin or near the surface of the skin when the device is employed. It is appreciated that an outer sleeve optionally forms an upper chamber that provides uniform distribution of vacuum pressure into and throughout the inner sleeve or the upper surface thereof.

An outer sleeve optionally terminates in or is integral with a collar. A collar is optionally in fluidic connection with a conduit. In some embodiments a collar is made of a material with increased rigidity relative to an outer sleeve.

An inventive device is optionally manufactured as a separate assembly or unitary piece so as to be associatable with a catheter prior to placement across the skin. An inventive device is optionally formed with a slot to accept a catheter or other instrument. An instrument is optionally slidable onto a catheter prior to inserting the catheter through the skin. Optionally, a catheter serves as a guide for an inventive instrument such that the instrument is slid onto a catheter following catheterization into the same insertion location. Engagement of the instrument prevents agents from entering the insertion point or will remove agents already in or under the insertion point.

In some embodiments, an inventive device is integral with a catheter or other percutaneous instrument.

An inventive complete instrument optionally includes a gasket, a conduit, a valve, and a vacuum source.

Without intending to be bound to a particular theory, a surface of an inventive device in contact with compromised skin for device insertion promotes intercalation of fibroblasts regardless of whether the surface is textured, coated, or a combination thereof so as to simultaneously promote orthological changes in the fibroblast from circulatory form to dendritic and/or stellate forms through a depth of more than one layer of fibroblast at a time and preferably more than five layers of fibroblasts simultaneously anchoring to the device and more preferably more than ten such layers of fibroblasts. Fibroblast orthological changes simultaneously in more than one layer of such cells serve to rapidly stabilize the percutaneous inventive device. In conjunction with the vacuum pressure draw during the process, infection risks are minimized and an inventive device is stabilized against pullout or other device motions relative to the surrounding dermal layers.

An inventive device optionally includes one or more gaskets or seals. A seal prevents vacuum pressure from escaping to the atmosphere or from drawing bodily fluid into the system from the subcutaneal end of the instrument. A gasket is optionally made from any material suitable for creating a seal around the circumference of a catheter. A gasket is illustratively made from silicon rubber, latex, nylon, or other polymeric materials. A gasket is optionally connected to or integral with an outer sleeve, an inner sleeve, a bandage, or a collar.

A conduit is optionally fluidly connected to an inner sleeve either via a gasket or direct connection. A conduit is optionally made of any material that will resist total collapse under vacuum pressures used with the invention.

A conduit is optionally transected by a valve. A valve is operable to engage, disengage, or adjust the vacuum pressure translated to the inner sleeve. A valve is optionally mechanically or electrically controlled. Any valve or valve system known in the art is operable herein. A valve is optionally positioned at the junction between the conduit and the instrument portions of the inventive device.

An inventive device is optionally connected to a vacuum source. A vacuum source can be any source operable for creating negative pressure in or around the device. A vacuum source is optionally a passive vacuum such as a vacuum tube or bottle, or an active vacuum source illustratively a mechanical pump, a syringe, or other vacuum source. A vacuum source optionally applies a continuous or intermittent negative pressure. The magnitude of the negative pressure is optionally adjustable, constant, or variable. In some embodiments an intermittent vacuum is used. Alternatively, a hydrodynamic draw agent is provided that draws fluid from the tissue surrounding through the sleeve via the conduit. A hydrodynamic draw source illustratively includes a super absorbent polymer such as sodium polyacrylate, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile; high osmotic pressure compositions, such as water soluble salts; and capillary flow draw agents such as dry silica, or other dry hydrophilic powders such cellulosic material.

The inventive device optionally includes a blood or other fluid detection system. A blood detection system is optionally a fluid sensing device. A fluid sensing device will optionally shut down the inventive device or reduce the negative pressure should too high a level of fluid pass through the conduit or otherwise into or around the inventive device. In some embodiments a fluid detection system will adjust the vacuum level to maintain fluid flow at a constant or variable rate. Should blood or other bodily fluid be detected at too high a rate, a detection system optionally reduces the vacuum level so as to reduce the rate or adjust type of fluid flow.

An inventive instrument optionally includes a bandage. A bandage illustratively forms a seal on the surface of the skin. In some embodiments a bandage forms a chamber on the surface of the skin surrounding the inner or outer sleeve. Although it is not absolutely necessary, a chamber allows rapid and uniform application of a vacuum pressure around the circumference of a catheter. A bandage is optionally a polymeric material, cloth, or other material known in the art.

In some embodiments an inventive device does not penetrate the skin. A bandage optionally is associated with a gasket or is itself made of material that is operable to itself function as a gasket around a catheter. The bandage is optionally made of material with sufficient rigidity so as not to totally collapse under the negative pressure of a vacuum on the epidermal side of the bandage. The bandage is optionally circular in outer or inner shape. This circular shape is entirely optional. Other shapes such as triangular, square, oval, or polygonal are similarly operable.

An inventive device is optionally a bandage surrounding a catheter or other instrument wherein the bandage is in fluidic communication with a valve or conduit. A negative pressure applied on the epidermal side of the bandage is optionally of sufficient force to seal the outer circumference of the bandage to the epidermal layer. The presence of the vacuum itself is optionally sufficient to reduce or eliminate movement of agents into the skin of the subject at the site of the catheter.

An optional adhesive is present on the bandage or on the epidermis for contact with the bandage. Adhesives are materials known in the art. Optionally, a bandage is integral with an instrument.

A diffuser or other porous material optionally surrounds a catheter and optionally rests on the epidermal layer. The device is optionally maintained in position by an adhesive that surrounds the catheter forming a seal sufficient to allow a vacuum to form around the insertion point. Alternatively, the vacuum itself produces a sufficient seal around the circumference of the instrument or between the epidermis and a diffuser to both hold it one or both in place and provide sufficient pressure to draw the device onto the skin surrounding the catheter.

In some embodiments several device diameters are operable. An inventive device optionally has an inner diameter and an outer diameter. The inner diameter of the device is optionally associated with the diameter of the percutaneous instrument. A larger percutaneous instrument generally will require a larger inner diameter of the device. Alternatively, a single inner diameter device is produced with removable and replaceable gaskets or seals that allow a wide range of catheter diameters or shapes to be used with the device.

In some embodiments the instrument is reusable. An inventive device is optionally autoclavable or otherwise sterilizable.

A system for reducing or eliminating catheter related infection is also provided. A system illustratively includes a plurality of inventive devices. A plurality of devices are optionally connected to a single vacuum source or a plurality of vacuum sources. A plurality of vacuum sources is optionally interconnected or otherwise simultaneously or individually adjustable to increase or decrease the vacuum pressure at one or more sites of catheter insertion.

A process for reducing, preventing, reversing, treating, or eliminating infection at a percutaneous insertion point is also provided. An inventive process illustratively includes applying a vacuum pressure around the circumference of a catheter or other percutaneous instrument. The vacuum pressure causes fluid to move away from the subdermal layers preventing infectious agents from entering the subdermal layer or preventing additional infectious agents from entering the region during treatment for catheter related infection.

An inventive device is shown generally at 10 in FIG. 1 and shows a sleeve 12 in fluid communication with the bore 14 of the conduit 16. The sleeve 12 is formed of materials as detailed above with respect to the inner sleeve and is characterized by a porous matrix 18 adjacent to a perforated outer surface 20 of the conduit 16. In operation, porous matrix 18 experiences strong vacuum or hydrodynamic forces created by a vacuum or hydrodynamic draw source, collectively depicted at 22. The matrix 18 has a rigidity sufficient to prevent collapse under the draw pressure as an operative requirement and thereby maintain vacuum or hydrodynamic through the matrix. A highly cross-linked polymeric substance, collagen, porous ceramic or metallic substances are particularly well suited to form matrix 18. A matrix 18 is appreciated to promote vacuum draw, such large pores are sized such that both bacteria and fibroblasts readily infiltrate such pores. Without intending to be bound by a particular theory, it is believed that deleterious agents within the matrix 18 are actively drawn into the conduit bore 14 or if capable of biological multiplication, inhibited from doing so by the forces exerted thereon by the source 22. The distal surface 24 of the sleeve 12 has an optional nanotexture 25, as detailed above to promote fibroblast pseudopod extension adherence yet are sufficiently small to discourage bacterial colonization. It is appreciated that the surface 24 experiences limited draw from the source 22. Optionally, an intermediate matrix 26 is provided between the matrix 18 and the surface 24. The matrix 26 preferably has a reduced pore size compared to matrix 18 and this attribute alone or in combination with a reduced cross-linking density reduces the draw forces created by source 22 in this region compared to that experienced in matrix 18. Alternatively, the matrix 26 has a like-pore size distribution relative to matrix 18, larger pore diameters relative to matrix 18 or a graded pore dimension as a function of thickness of matrix 26. The matrix 26 is formed of the same implant compatible material as matrix 18 or another implant compatible material. To better depict the sleeve porosity, the right side of FIG. 1 only shows a single pore of matrix 26 in fluid communication with pore of matrix 18. A higher degree of pore collapse associated with vacuum draw through the matrix 26 is not only tolerated but is believed to promote rapid stabilization of the device 10. Accordingly, a program of source draw is optionally provided that varies the strength of the vacuum or osmotic pressure applied to the matrix 18 and by extension to matrix 26 as a function of time. The pore size in optional matrix 26 is of a size that allows circulating fibroblasts to infiltrate matrix 26 and thereby initiate the healing process through formation of an interconnected network of fibroblasts and other cells and compounds needed for tissue granulation. Typical cross-sectional dimensions of pores in the matrix 26 are between 3 and 50 circulating fibroblast diameters. It is further appreciated that the infiltration of the matrix 26 by fibroblasts operative to dimensionally extend the device stabilization from a single layer of fibroblasts seen in a non-porous surface implant to a region corresponding to the thickness of the matrix 26. One of skill in the art will appreciate that the strength of the vacuum or osmotic draw from source 22 is readily adjusted to promote infiltration into optional matrix 26 to speed stabilization. It is appreciated that the application of draw forces via source 22 in addition to inhibiting agents and promoting fibroblast infiltration also serves the tissue-scale function of adhering the body tissue T surrounding the device 10 in a fixed position in contact with device 10 so as to form a stable interface therebetween. The resulting interface is superior for the granulation process relative to conventional sutures or adhesive bandages. It is appreciated that the matrix 18 and the matrix 26 with a nanotextured surface 24 are integral, or alternatively are formed as contiguous separate layers as detailed above with respect to inner and outer sleeves. A coating substance 27 optionally overcoats the surface 24, with coating substances illustratively include cellular ingress scaffolding, as will be further detailed below. The coating substance has a tissue contacting surface 29 that is optionally nanotextured.

An inventive device is further detailed in FIG. 2 generally at 30 where like numerals correspond to the meaning imparted thereto with respect to the aforementioned figure and specification text. Device 30 has a central medical appliance that is depicted as a cannula 34 shown in the context of providing fluid communication between a medical appliance 34 with subject vein V. The medical instrument 34 illustratively includes a catheter, cannula, pin, or wire or other percutaneous instrument with specific versions thereof including a Steinman pin and a Kirschner wire. The device 30 is percutaneous through the epidermis, dermis, and subcutaneous layers that are denoted at E, D, and S, respectively. The device 30 has an inner sleeve 12a that corresponds to sleeve 12 detailed with respect to FIG. 1 with the exception of varying in dimensionality. The inner sleeve 12a has a porous matrix 18 in fluid communication with the vacuum or hydrodynamic draw source 22. Matrix 26 is optionally present intermediate between matrix 18 and surface 24. Preferably, a coating substance 27 overlies the surface 24. An outer sleeve 36 engages the medical appliance 34 at a vacuum seal 36 and forms fluid communication with a vacuum or hydrodynamic draw source 22 via conduit 38. The outer sleeve 33 of device 30 is shown in FIG. 2 as the outer sleeve 33 wholly enveloping inner sleeve 12a and serves as an introducer preventing the transmission of skin bacteria to the wound created by placement of the device 30 and after positioning as shown in FIG. 2, the outer sleeve 33 is retracted relative to the appliance 34 and inner sleeve 12a to a position preferably just above epidermis E thereby allowing the source 22 to draw fluid through the then exposed surface 24 and that of an optional coating 27 to the surrounding tissue as well as the draw created source 22. It is appreciated that the relative dimensions of attributes depicted in FIG. 2 are distorted for visual clarity.

An inventive device is depicted in FIG. 3 generally at 40 where like numerals correspond to the meaning ascribed thereto in the aforementioned figures. The device 40 varies from that depicted in FIG. 2 only in that the outer sleeve 44 is preformed to not extend the full linear extent of the inner sleeve 12a and instead forms an insertion stop against the epidermis, E.

Figure 4:
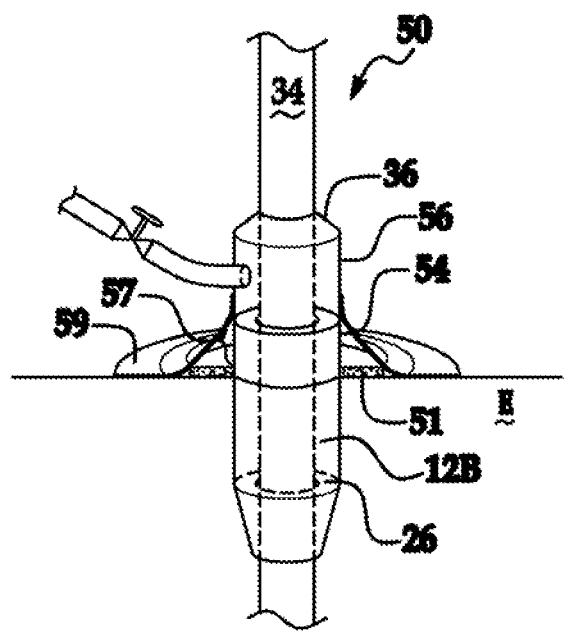
FIG. 4 is a perspective view of an inventive device employed with a bandage providing a pressure seal to the outer surface of the skin.

FIG. 4 is a perspective, partial cutaway view of an inventive device 50 in which like numerals having the meanings ascribed thereto in the aforementioned figures. Percutaneous medical appliance 34 has a vacuum seal or gasket at 36 between a conduit 56 and a medical appliance 34. The conduit 56 is in fluid communication with an inner sleeve 12b that is otherwise the same as sleeves 12 and 12a except for dimensionality. It is appreciated that inner sleeve 12b optionally includes matrix 26 thereover, a coating substance 27, or a combination thereof. Vacuum or hydrodynamic draw of the inner sleeve 12b by a conduit 56 requires vacuum draw to be precluded from region 57 of porous inner sleeve 12b denoted at 57. Preferential vacuum draw through region 57 relative to subdermal portions of inner sleeve 12b is accomplished through adherence of a gas-tight bandage 59 to the outer surface of the epidermis E. It is appreciated that bandage 59 is used as a substitute for, or in combination with, an outer sleeve 54 forming a gas-tight seal with conduit 56 so as to achieve fluid communication between a source 22 and the subcutaneous portions of inner sleeve 12b. Optionally, a diffuser constituting an open cell foam material or woven material 51 is positioned intermediate between the outer surface of the epidermis E and the bandage 59 to moderate vacuum draw therethrough.

Figure 5:
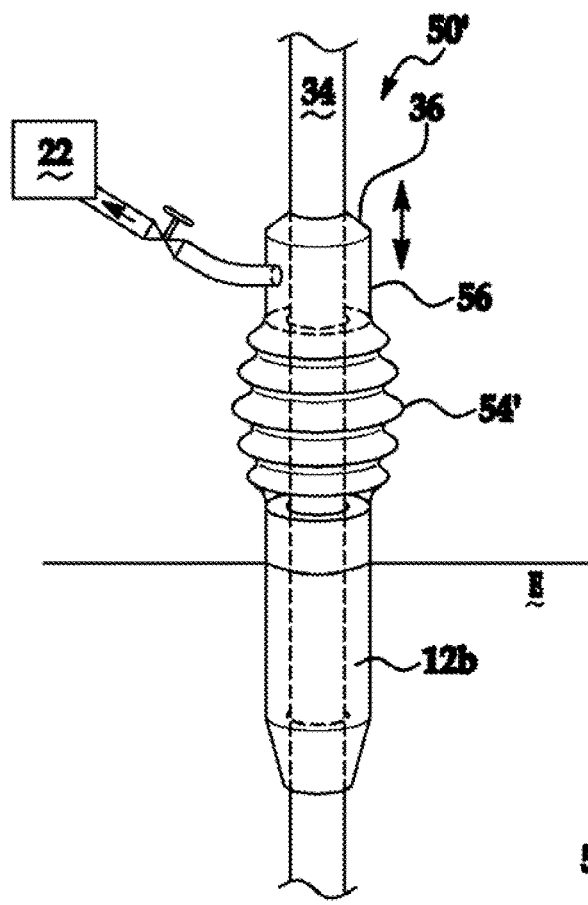
FIG. 5 is a perspective view of an inventive device with relative dimensions of aspect exaggerated for visual clarity with an expandable outer sleeve.

An inventive device is shown generally at 50' in FIG. 5, where like numerals used therein have the meaning ascribed thereto with respect to the aforementioned figures. The device 50' has all the attributes of device 50 save for an outer sheath 54' having an expanded bellows-like construct providing a mode of varying the linear extent of the outer sleeve 54'. It is appreciated that the conduit 56 is readily constructed to be slidable relative to appliance 34 and in conjunction with outer sleeve 54'.

Figure 6:
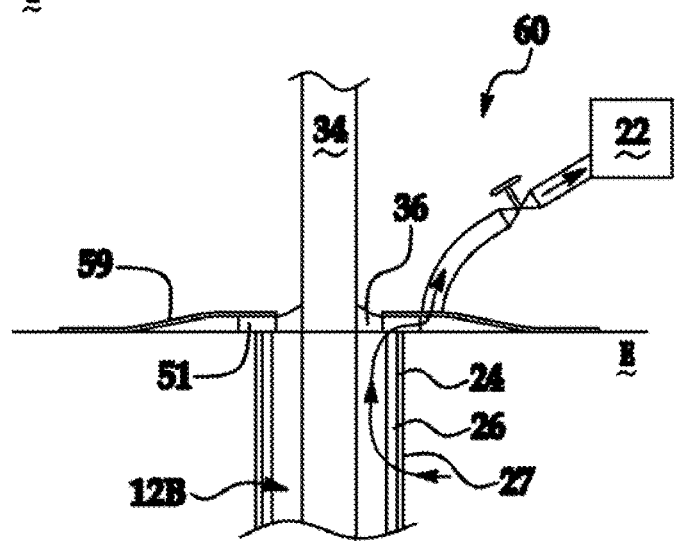
FIG. 6 is a cross-sectional view of the relative dimensions of aspects exaggerated for visual clarity depicting a pressure seal formed against the outer surface of the skin with resort to a gasket and a bandage.

FIG. 6 is a cross-sectional view of an inventive device, shown generally at 60, where like numerals have the meaning ascribed thereto with respect to the aforementioned figures. An inner sleeve 12b has a gasket or seal 36 around the appliance 34 that contacts the outer layer of epidermis E. A diffuser in the form of an annulus surrounds the gasket and is sealed against drawing exogenous air to the source 22 via bandage 59. A vacuum draw through subject tissue, optional coating 26 and via inner sleeve 12b, diffuser 51 through source 22 is depicted.

Figure 7A:
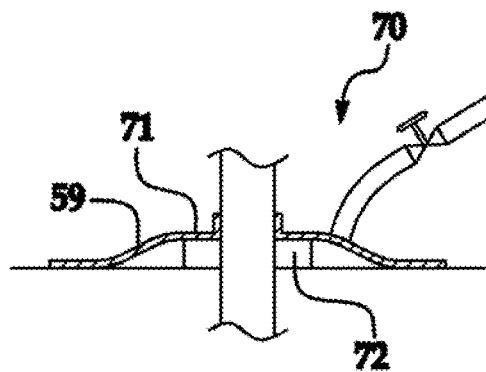
FIG. 7A is a cross-sectional view of an inventive device with relative dimensions of aspect exaggerated for visual clarity depicting a silicon collar and a plastic base forming a slidable pressure-tight seal against the outer surface of the skin.
Figure 7B:
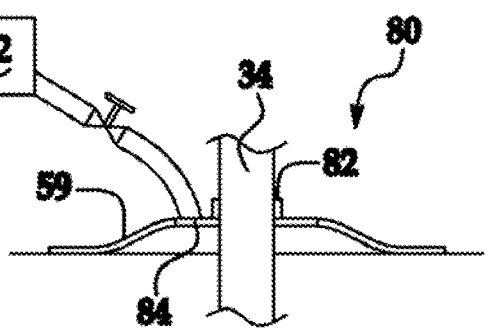
FIG. 7B is a cross-sectional view of an inventive device with relative dimensions of aspect exaggerated for visual clarity depicting a silicon collar and a plastic base forming a slidable pressure-tight seal against the outer surface of the skin.

An inventive device is readily provided in the form of a kit with a variety of sizes of gaskets, bandages, and diffusers to provide a skintight seal such that vacuum draw communication is produced between the skin surrounding an inventive device through an inner sleeve to a source 22. FIGS. 7A and 7B depict an inventive device generally at 70 and 80, respectively, where like numerals correspond to the meaning ascribed thereto with respect to the aforementioned figures. A collar formed of a material such as silicone 72 or 82 has an annular split allowing the collar to slide along the length of medical appliance 34 and preferably remote from the surface of the epidermis E. A plastic base 74 or 84 extends outward so that a bandage 59 is readily secured and sealed to the collar 72 or 82.

FIGS. 8A and 8B depict the percutaneous components of inventive device with relative dimensions of aspect exaggerated for visual clarity where like numerals have the meaning ascribed thereto with respect to the aforementioned figures. A flanged inner sleeve 12c has the same attributes as inner sleeve 12, 12a, and 12c and varies therefrom only in shape. The inner sleeve 12c is formed of materials as detailed above and is characterized by a large and rigid pore matrix 18 in fluid communication to a vacuum source 22. Sleeve 12c has a surface 24 that optionally nanotextured to promote fibroblast adhesion. The surface 24, like the surfaces of any of the aforementioned sleeves 12, 12a, or 12b is optionally decorated with has a pattern of contoured cell-conveying channels 82. It is appreciated that the channels can take a variety of forms. It is appreciated that an operative device typically would have a pattern of channels 82 circumferentially decorating the surface 24. Channel patterns operative herein include any pattern that disfavors bacterial pocket formation. The channel 82 is formed by methods such as imprinting, embossing, molding or machining into the sleeve 12c. Preferably, the sleeve 12c is a nanotextured and decorated with channels 82. A channel 82 according to the present invention preferably has dimensions on the order of two to ten times the diameter of a fibroblast that is equivalent to 20 to 300 microns since a fibroblast has a diameter from 10 to 15 microns. More preferably, a channel 82 has a width of between 30 and 120 microns. Most preferably, channel 82 is devoid of discontinuities and acute angles that disfavor cellular planarization and adhesion. A parabolic cross section is exemplary of a channel facilitating fibroblast growth. Preferably, the transition between the channel 82 and the adjacent region of surface 24 is devoid of discontinuities and acute angles that disfavor cellular planarization and adhesion. It is appreciated that inner sleeve 12b optionally includes matrix 26 thereover, a coating substance 27, or a combination thereof. The tissue contacting surface 29 of substance 27 is optionally nanotextured. A velour 84 optionally encompasses a portion of the sleeve 12c. The velour 84 is illustratively formed of DACRON®, or to the implantable polymeric material. The velour 84 is also optionally biodegradable.

FIG. 9 depicts an inventive device generally at 100 where like numerals correspond to the meaning ascribed thereto with respect to the aforementioned figures. A cap 102 is formed of a material such as silicone, a polymer or a metal and serves to keep debris from entering the device 100. Preferably, the cap 102 is remote from the surface of the epidermis E. The medical appliance 34 depicted as a catheter and vacuum or hydrodynamic draw tubing 104 pass through complementary openings 106 and 108, respectively formed in the cap 102. The tubing 104 provides fluid communication between a vacuum or hydrodynamic draw source 22 and an inner sleeve 12d that has the same attributes as inner sleeve 12, 12a, 12b, and 12c and varies therefrom only in shape. The inner sleeve 12d is formed of materials as detailed above and is characterized by a large and rigid pore matrix 18 in fluid communication to a vacuum source 22 such that the source 22 draws tissue fluid and fibroblasts into the sleeve 12d. Sleeve 12d has a surface 24 that optionally nanotextured to promote fibroblast adhesion. The surface 24, like the surfaces of any of the aforementioned sleeves 12, 12a, or 12b is optionally decorated with has a pattern of contoured cell-conveying channels as shown in FIGS. 8A and 8B. It is appreciated that inner sleeve 12d optionally includes matrix 26 thereover, a coating substance 27, or a combination thereof. The coating 27 is appreciated to need not cover the entire surface 24. The tissue contacting surface 29 of substance 27 is optionally nanotextured. A flange 112 is provided to stabilize the implanted device 100 within the subcutaneous layer S. The flange 112 is constructed from materials and formed by methods conventional to the art. For example, those detailed in U.S. Pat. Nos. 4,634,422; 4,668,222; 5,059,186; 5,120,313; 5,250,025; 5,814,058; 5,997,524; and 6,503,228.

Figure 10:
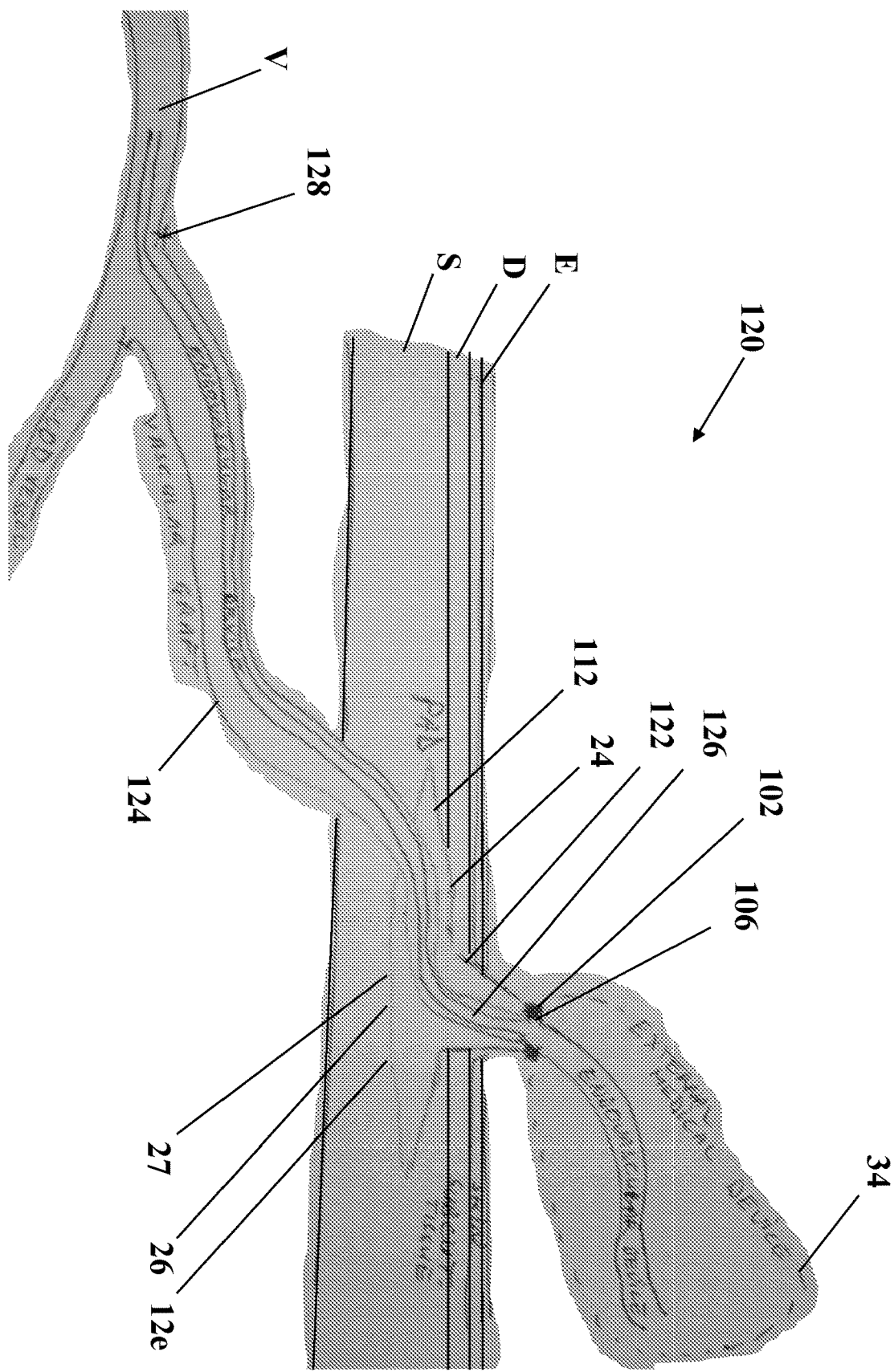
FIG. 10 is a cross-sectional view of an inventive device with relative dimensions of aspects exaggerated for visual clarity depicting a vascular graft secured thereto.

FIG. 10 depicts an inventive device generally at 120 where like numerals correspond to the meaning ascribed thereto with respect to the aforementioned figures. While the invention is further detailed in FIGS. 10 and 11 in the context of single and dual conduit devices coupled to blood vessels as exemplary lumens within a patient, it is appreciated that other applications for the present invention include peritoneal dialysis (abdominal cavity), neural implants (patient brain), osseous integrated implants (medullary cavity or intra-osseous), colostomy (colon), urostomy (ureter), where the lumen is provided in parentheses. The single channel vascular access device 120 is a percutaneous access device (PAD) 122 coupled to a luminal (vascular) graft 124 so as to permit extra-corporeal access to the luminal (vascular) system. The graft 124 secured to the PAD 122 permits a physician to reversible connect to, or introduce a medical device, such as a long-term intra-aortic balloon pump, to the vascular system or another medical device as detailed above. A cap 102 is formed of a material such as silicone, a polymer or a metal and serves to keep debris from entering the PAD 122. Preferably, the cap 102 is remote from the surface of the epidermis E. The external medical appliance 34 and/or an endovascular device 126 passes through opening 106 formed in the cap 102 and travels via a graft 124 to a patient's lumen (vein V). The graft 124 is attached via sutures 128 to a patient's lumen (vein V). The surface 24 of the PAD 122 is optionally nanotextured to promote fibroblast adhesion. The surface 24, like the surfaces of any of the aforementioned sleeves 12, 12a, or 12b is optionally decorated with has a pattern of contoured cell-conveying channels as shown in FIGS. 8A and 8B. It is appreciated that inner sleeve 12e optionally includes matrix 26 thereover, a coating substance 27, or a combination thereof. The coating 27 is appreciated to need not cover the entire surface 24. The tissue contacting surface of substance 27 is optionally nanotextured. A flange 112 is provided to stabilize the implanted device 122 within the subcutaneous layer S. The flange 112 is constructed from materials and formed by methods conventional to the art. For example, those detailed in U.S. Pat. Nos. 4,634,422; 4,668,222; 5,059,186; 5,120,313; 5,250,025; 5,814,058; 5,997,524; and 6,503,228.

Figure 11:
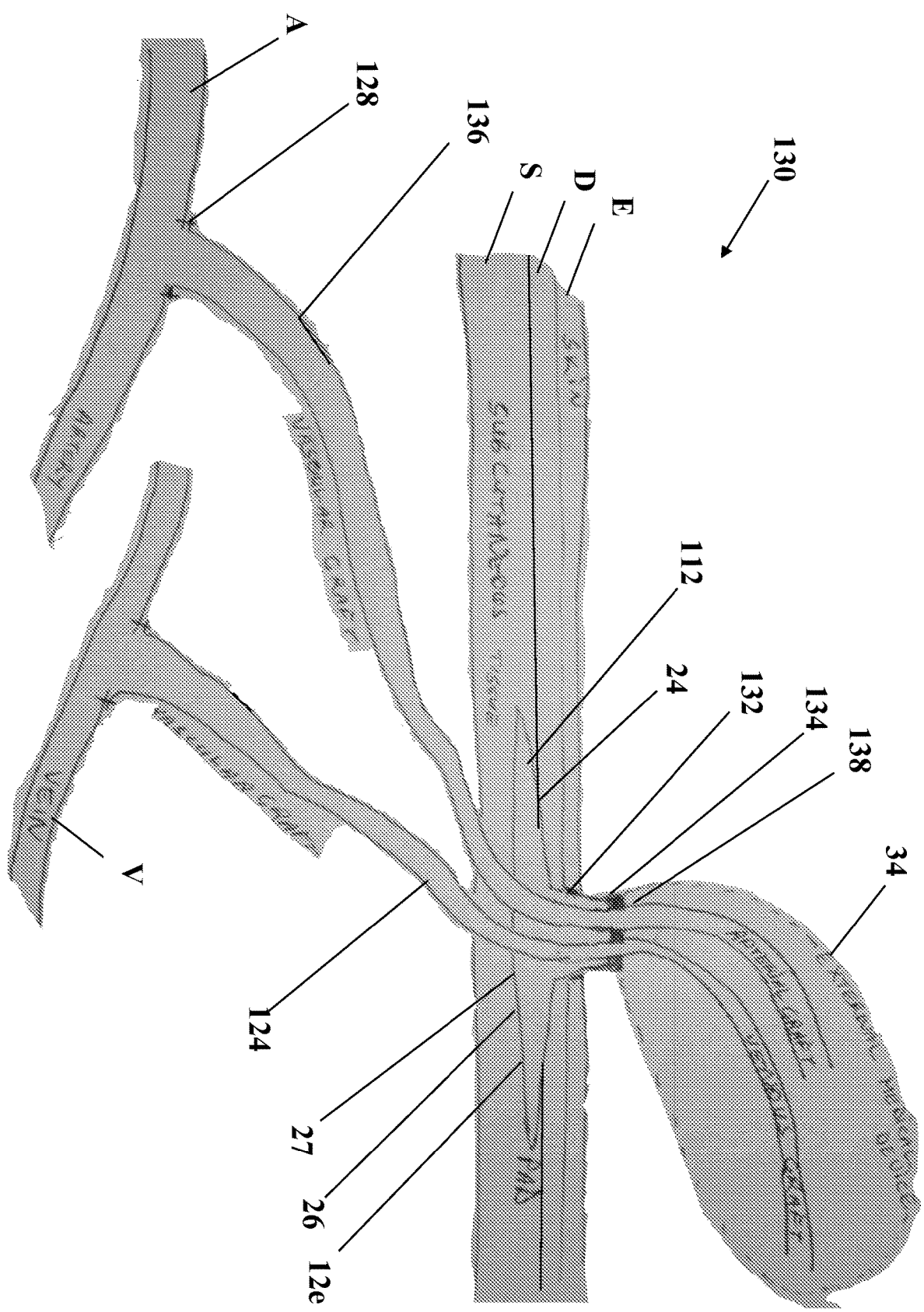
FIG. 11 is a cross-sectional view of an inventive device with relative dimensions of aspects exaggerated for visual clarity depicting a dual lumen vascular access port for simultaneous access to two locations of the vascular system.

FIG. 11 depicts an inventive device generally at 130 where like numerals correspond to the meaning ascribed thereto with respect to the aforementioned figures. The dual lumen luminal (vascular) access device 130 is a percutaneous access device (PAD) 132 with dual ports coupled to a luminal (venous) graft 124 and arterial graft 136 so as to permit extra-corporeal access to the vascular system, as well as, simultaneous access to two locations of the vascular system. Examples of dual access applications may include extra-corporeal membrane oxygenation, dialysis, extracorporeal cardiac assist, etc. A cap 134 with dual openings is formed of a material such as silicone, a polymer or a metal and serves to keep debris from entering the PAD 132. Preferably, the cap 134 is remote from the surface of the epidermis E. The external medical appliance 34 and/or an endovascular device 126 passes through dual openings 138 formed in the cap 134 and travels via a vascular graft 124 to a patients vein V and arterial graft 136 to artery A. The vascular graft 124 and a second luminal (arterial) graft 136 are attached via sutures 128 to a patient's vein V and artery A, respectively. The surface 24 of the PAD 132 is optionally nanotextured to promote fibroblast adhesion. The surface 24, like the surfaces of any of the aforementioned sleeves 12, 12a, or 12b is optionally decorated with has a pattern of contoured cell-conveying channels as shown in FIGS. 8A and 8B. It is appreciated that inner sleeve 12e optionally includes matrix 26 thereover, a coating substance 27, or a combination thereof. The coating 27 is appreciated to need not cover the entire surface 24. The tissue contacting surface of substance 27 is optionally nanotextured. A flange 112 is provided to stabilize the implanted device 132 within the subcutaneous layer S. The flange 112 is constructed from materials and formed by methods conventional to the art. For example, those detailed in U.S. Pat. Nos. 4,634,422; 4,668,222; 5,059,186; 5,120,313; 5,250,025; 5,814,058; 5,997,524; and 6,503,228.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for reducing, preventing, reversing, treating, or eliminating infection at a percutaneous insertion site comprising:
    inserting subcutaneously a percutaneous access device (PAD) having a bore, said PAD having an upper portion that remains external to a patient where the upper portion is covered by a cap, said cap having an opening over said bore, said bore configured to be coupled to a proximal end of a luminal graft and where a distal end of the luminal graft is attached to a patient lumen;
    stabilizing the luminal graft with said PAD when an external medical device is inserted through said opening in said cap and through said bore in said PAD and to the patient lumen via the luminal graft; and
    forming a seal around the luminal graft at said cap.

2. The process of claim 1 further comprising applying an external vacuum or hydrodynamic pressure in fluid communication with a porous inner sleeve, wherein said porous inner sleeve is in fluid communication with said bore in said PAD.

3. The process of claim 2 further comprising an outer sleeve at least partially surrounding said inner sleeve; said outer sleeve fluidly connected to said bore via said porous inner sleeve.

4. The process of claim 3 further comprising treating said outer sleeve with a coating substance to encourage fibroblast attachment.

5. The process of claim 3 further comprising texturing said outer sleeve to encourage fibroblast attachment.

6. The process of claim 3 wherein said outer sleeve further comprises at least one compound of a growth factor, extracellular matrix factors, fibroblast receptors, fibronectin, laminectin, RGD factor, dexamethasone, or combinations thereof.

7. The process of claim 2 further comprising treating said inner sleeve with a coating substance to encourage fibroblast attachment.

8. The process of claim 2 further comprising texturing said inner sleeve to encourage fibroblast attachment.

9. The process of claim 2 wherein said inner sleeve further comprises at least one compound of a growth factor, extracellular matrix factors, fibroblast receptors, fibronectin, laminectin, RGD factor, dexamethasone, or combinations thereof.

10. The process of claim 1 further comprising stabilizing said PAD within the subcutaneous layer of the patient via a flange.

11. The process of claim 1 wherein said PAD is a peritoneal device adapted for insertion of the external medical device through the luminal graft to the patient lumen, the patient lumen being an abdominal cavity.

12. The device of claim 1 wherein said PAD is an endovascular device adapted for insertion of the external medical device through the luminal graft to the patient lumen, the patient lumen being a blood vessel.

13. The process of claim 1 wherein said PAD is a neural implant device and the patient lumen is in a patient brain.

14. The process of claim 1 wherein said PAD is a bone implant device adapted for insertion of osseous integrated implants to be inserted into the patient lumen, the patient lumen being a bone medullary cavity.

15. The process of claim 1 wherein said PAD is a colostomy device and the patient lumen being a colon.

16. The process of claim 1 wherein said PAD is a urostomy device and the patient lumen being a ureter.

17. A process for reducing, preventing, reversing, treating, or eliminating infection at a percutaneous insertion site comprising:

inserting subcutaneously a percutaneous access device (PAD), said PAD having an upper portion that remains external to a patient where the upper portion is covered by a cap, said cap having a first opening and a second opening, said PAD having a first Pore configured to be coupled to a proximal end of a first luminal graft and where a distal end of the first luminal graft is attached to a first patient lumen, and a second bore configured to be coupled to a proximal end of a second luminal graft and where a distal end of the second luminal graft is attached to a second patient lumen;

stabilizing the first and second luminal grafts with said PAD when separate external medical devices are individually inserted through one of said first and second openings in said cap and through said first and second bores in said PAD and to the first patient lumen and the second patient lumen via-the first luminal graft and second luminal graft grafts, respectively; and forming a seal around the first and second luminal grafts at said cap.

18. The process of claim 17 wherein the first patient lumen is a venous blood vessel, and the second patient lumen is an arterial blood vessel.

* * * * *